United States Patent
Farnan

(10) Patent No.: US 10,688,230 B2
(45) Date of Patent: Jun. 23, 2020

(54) MALLEABLE CANNULA

(71) Applicant: CircuLite, Inc., Saddle Brook, NJ (US)

(72) Inventor: Robert C. Farnan, Ridgewood, NJ (US)

(73) Assignee: CircuLite, Inc., Teaneck, NJ (US)

( * ) Notice: Subject to any disclaimer, the term of this patent is extended or adjusted under 35 U.S.C. 154(b) by 583 days.

(21) Appl. No.: 13/788,039

(22) Filed: Mar. 7, 2013

(65) Prior Publication Data
US 2014/0257018 A1    Sep. 11, 2014

(51) Int. Cl.
*A61M 1/10*    (2006.01)
*A61M 1/12*    (2006.01)

(52) U.S. Cl.
CPC ............. *A61M 1/1008* (2014.02); *A61M 1/10* (2013.01); *A61M 1/12* (2013.01)

(58) Field of Classification Search
CPC ....... A61B 5/48; A61B 5/6846; A61B 5/6867; A61B 5/6869; A61M 25/00; A61M 27/00; A61M 29/00; A61M 31/00; A61M 37/00; A61M 99/00; A61M 25/0051
See application file for complete search history.

(56) References Cited

U.S. PATENT DOCUMENTS

| | | |
|---|---|---|
| 4,639,252 A | 1/1987 | Kelly et al. |
| 4,976,688 A | 12/1990 | Rosenblum |
| 5,329,923 A | 7/1994 | Lundquist |
| 5,454,787 A | 10/1995 | Lundquist |
| 6,001,056 A | 12/1999 | Jassawalla et al. |
| 6,016,848 A | 1/2000 | Egres, Jr. |
| 6,022,343 A | 2/2000 | Johnson et al. |
| 6,066,125 A | 5/2000 | Webster, Jr. |
| 6,152,911 A | 11/2000 | Giannoble |
| 6,544,215 B1 | 4/2003 | Bencini et al. |
| 6,976,979 B2 | 12/2005 | Lawrence et al. |
| 7,637,901 B2 | 12/2009 | Lawrence et al. |
| 2002/0183584 A1 | 12/2002 | Shannon et al. |

(Continued)

FOREIGN PATENT DOCUMENTS

| | | |
|---|---|---|
| EP | 1656963 A1 | 5/2006 |
| WO | 2005094525 A2 | 10/2005 |
| WO | 2011035327 A1 | 3/2011 |

OTHER PUBLICATIONS

European Patent Office, International Search Report and Written Opinion in PCT Application Serial No. PCT/US2014/013709, dated Apr. 7, 2014.

(Continued)

*Primary Examiner* — Eric D. Bertram
*Assistant Examiner* — Elizabeth K So
(74) *Attorney, Agent, or Firm* — Christopher & Weisberg, P.A

(57) ABSTRACT

A malleable cannula. The malleable cannula includes a polymeric jacket and a malleable member. The malleable member, being surrounded by the jacket, includes a proximal end, a distal end, and a lumen extending therebetween and along a lengthwise axis of the malleable cannula. The malleable member further includes a longitudinal strut that is parallel to the lengthwise axis and a plurality of transverse struts coupled to and extending laterally away from the longitudinal strut and at least a portion of the lumen. The malleable member is configured to assume and maintain a shape of the malleable cannula.

14 Claims, 6 Drawing Sheets

(56) References Cited

U.S. PATENT DOCUMENTS

| | | | |
|---|---|---|---|
| 2003/0069522 A1* | 4/2003 | Jacobsen | A61M 25/0013 600/585 |
| 2010/0036364 A1* | 2/2010 | Wubbeling | A61M 25/0051 604/528 |

OTHER PUBLICATIONS

European Patent Office, International Preliminary Report on Patentability in PCT Application Serial No. PCT/US2014/013709, dated Jun. 2, 2015.

Communication pursuant to Article 94(3) EPC, dated Nov. 15, 2018, for corresponding European Application No. 14 703 752.7, 7 pages.

\* cited by examiner

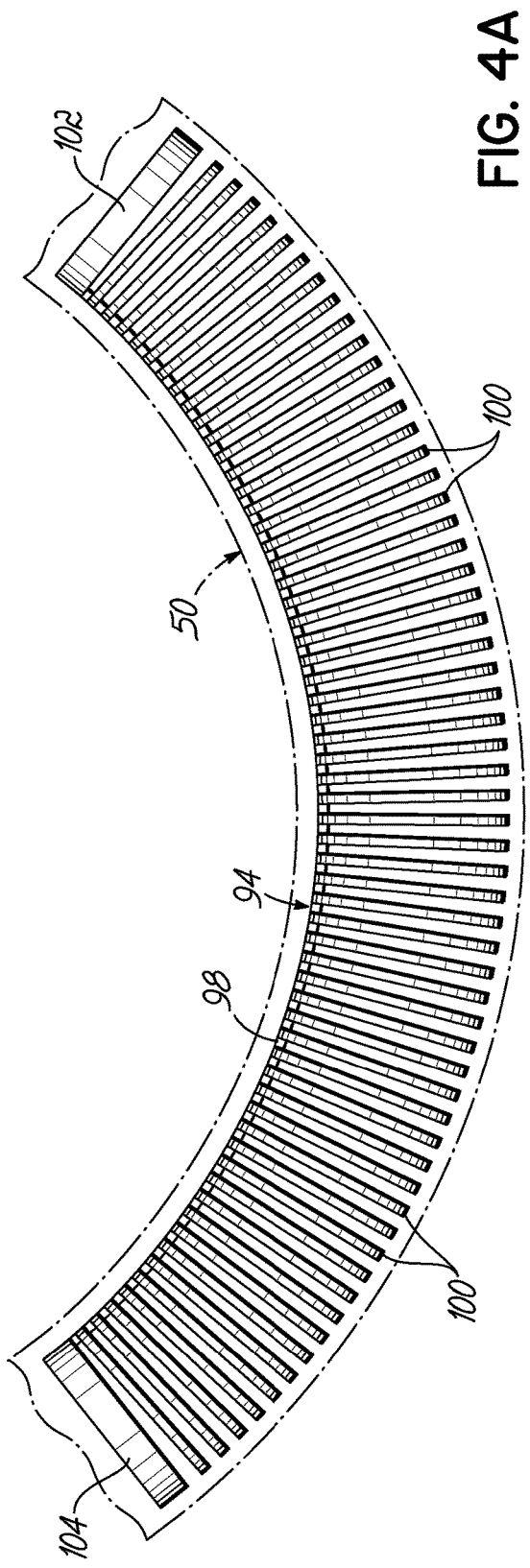
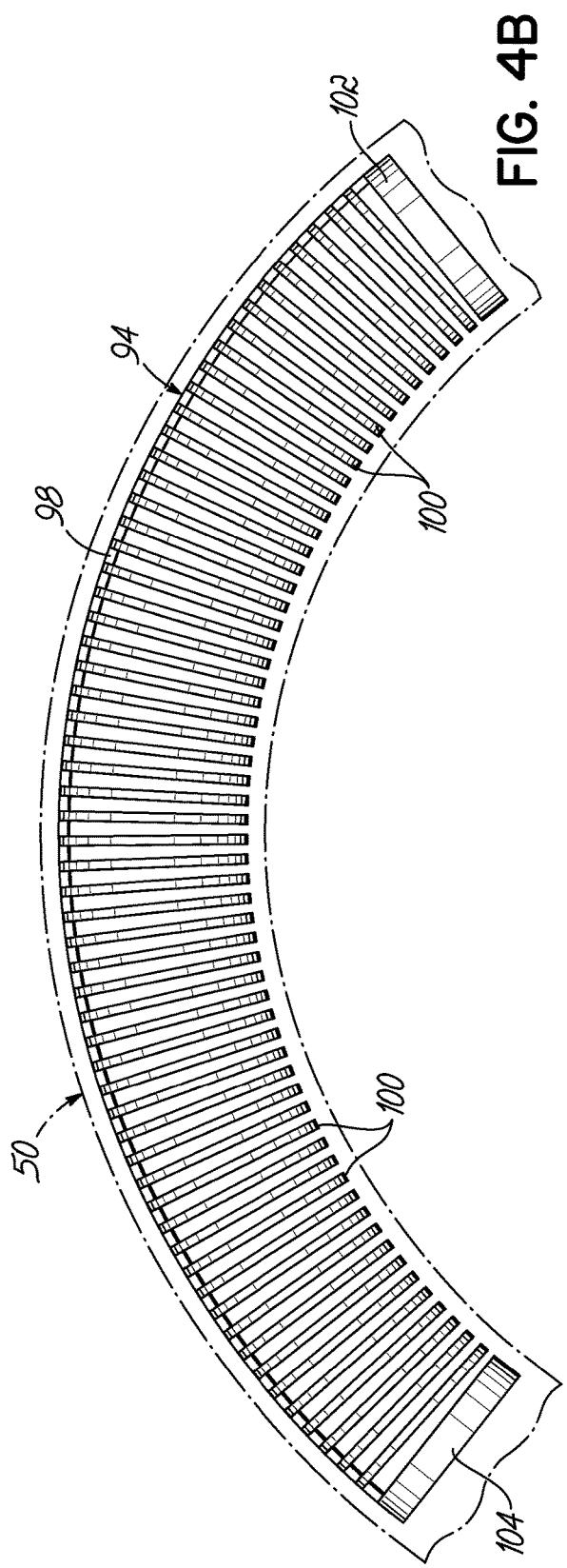
FIG. 4A
FIG. 4B

MALLEABLE CANNULA

FIELD OF THE INVENTION

The present invention relates generally to medical devices for assisting in the conduction of bodily fluids and, more particularly, to cannulae for use in moving bodily fluids.

BACKGROUND

Various devices and methods have been utilized to assist in conducting bodily fluids. Blood pumps with inflow and outflow cannulae assist the heart in circulating blood in a patient experiencing congestive heart failure, for example, when a transplant organ is not available or the patient is not a suitable candidate for transplant. The blood pump may be fluidically attached to the heart and/or other vascular structure by the cannulae and then located remotely within the patient or left to remain external to the patient.

The conventional cannula design for these procedures is a molded polymeric structure that may include a reinforcement structure, for example, a metallic or polymeric braid or coil, for reducing the likelihood of kink formation. While this solution has been effective for its intended purpose, the reinforcement structure limits the ability of the physician to customize the shape of the cannula to a particular patient's anatomy.

In addition to the reinforcement structure, some cannulae include a malleable device, such as a tube or rod, extending the length of the cannula for retaining a shape of the cannula. However, some of these known, conventional malleable devices require assembly by the physician or may move relative to the reinforcement structure. As a result, the shape of the cannula may inadvertently be altered and/or the cannula material may become damaged. Therefore, there remains a need for a cannula design that addresses one or more of these issues.

SUMMARY

In accordance with one embodiment of the present invention, a malleable cannula is described. The malleable cannula includes a polymeric jacket and a malleable member. The malleable member, being surrounded by the jacket, includes a proximal end, a distal end, and a lumen extending therebetween and along a lengthwise axis of the malleable cannula. The malleable member further includes a longitudinal strut that is parallel to the lengthwise axis and a plurality of transverse struts coupled to and extending laterally away from the longitudinal strut and at least a portion of the lumen. The malleable member is configured to assume and maintain a shape of the malleable cannula.

In accordance with one embodiment of the present invention, a malleable cannula is described. The malleable cannula includes a liner, a malleable member, and a jacket. The liner has a proximal end, a distal end, and a lumen extending between the proximal and distal ends and along a lengthwise axis of the cannula. A jacket surrounds the liner. The malleable member includes a longitudinal strut that is parallel to the lengthwise axis and a plurality of transverse struts coupled to and extending laterally away from the longitudinal strut and at least a portion of the lumen. The malleable member is configured to assume and maintain a shape of the malleable cannula.

Still another embodiment of the present invention is directed to a cannula that is configured to move fluids between a pump and the circulatory system of a patient. The cannula includes a malleable member and a jacket. The malleable member, being surrounded by the jacket, includes a proximal end, a distal end, and a lumen extending therebetween and along a lengthwise axis of the malleable cannula. The malleable member further includes a longitudinal strut that is parallel to the lengthwise axis and a plurality of transverse struts coupled to and extending laterally away from the longitudinal strut and at least a portion of the lumen. The malleable member is configured to assume and maintain a shape of the malleable cannula. A proximal end of the jacket is configured to be connected to the pump, and a distal end of the jacket is configured to be connected to the circulatory system.

According to one embodiment of the present invention, an inflow cannula for moving fluids from a chamber of the heart to a pump includes a malleable member and a jacket. The malleable member, being surrounded by the jacket, includes a proximal end, a distal end, and a lumen extending therebetween and along a lengthwise axis of the malleable cannula. The malleable member further includes a longitudinal strut that is parallel to the lengthwise axis and a plurality of transverse struts coupled to and extending laterally away from the longitudinal strut and at least a portion of the lumen. The malleable member is configured to assume and maintain a shape of the malleable cannula. A proximal end of the jacket is configured to be connected to the pump, and a distal end of the jacket is configured to be connected to the circulatory system. A distally-positioned tip is coupled to a distal end of the jacket and configured to be positioned across a wall of the heart while a proximally-positioned hub is coupled to a proximal end of the jacket and configured to secure the inflow cannula to the pump

BRIEF DESCRIPTION OF THE DRAWINGS

FIG. 4A is a side-elevational view of the malleable member bent in an upwardly-oriented direction, with the cannula environment shown in phantom.

FIG. 4B is a side-elevational view of the malleable member bent in a downwardly oriented direction, with the cannula environment shown in phantom.

DETAILED DESCRIPTION

While the various embodiments of the present invention may be useful for procedures involving any organ or cavity within the body, including, for example, the kidneys, the bladder, the stomach, or the heart, the particular embodiments of the present invention illustrated herein are drawn specifically to applications with the heart.

Figure 1:
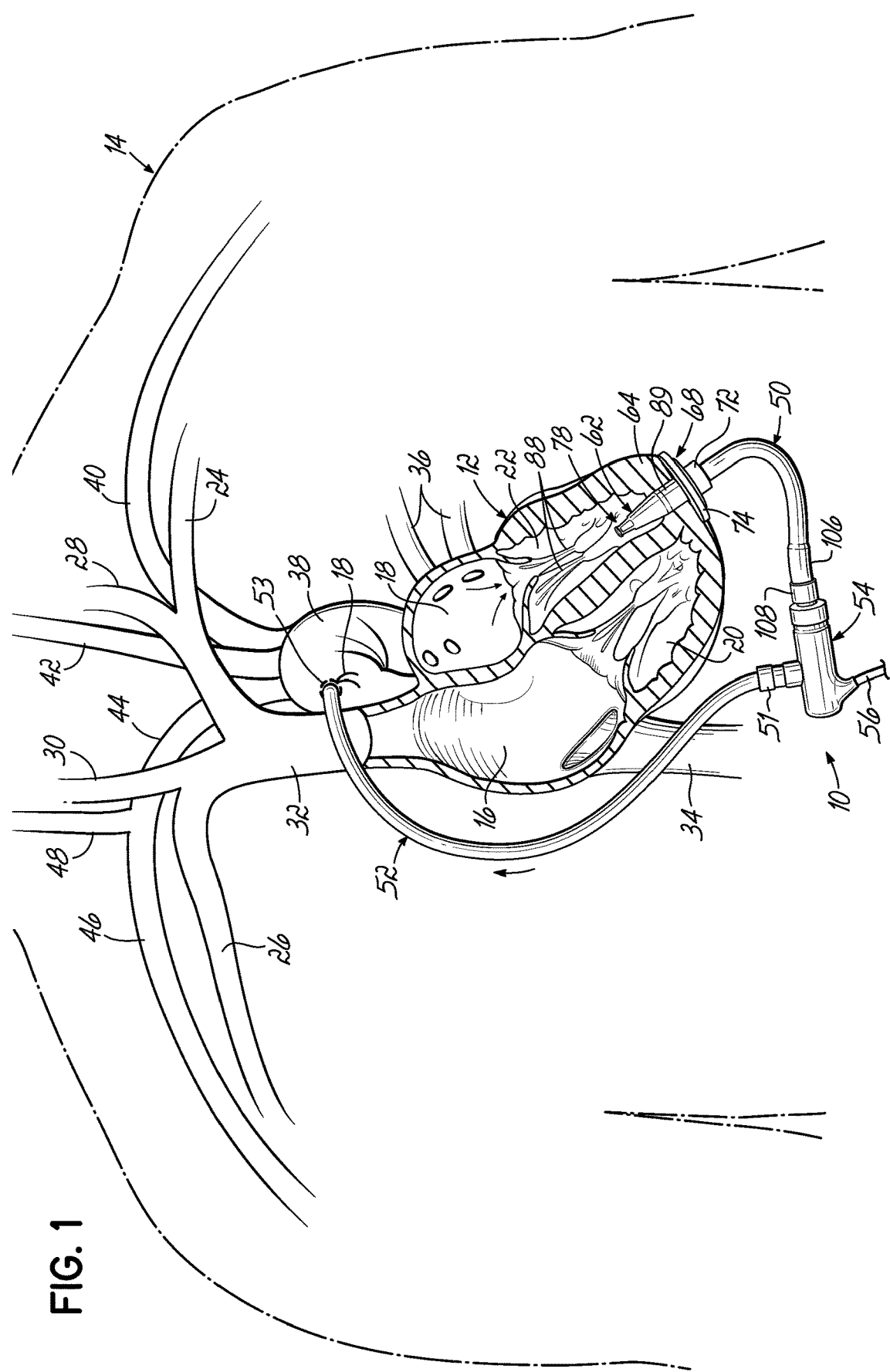
FIG. 1 is a schematic representation of chest anatomy and illustrates a cardiac assist system having an inflow cannula extending between the heart and a pump, the cannula being constructed in accordance with one embodiment of the present invention.

FIG. 1 illustrates a circulatory assist device 10 implanted in a patient 14. For illustrative purposes, certain anatomy is shown, including, the heart 12 of the patient 14 having a right atrium 16, a left atrium 18, a right ventricle 20, and a left ventricle 22. Blood from the left and right subclavian veins 24, 26 and the left and right jugular veins 28, 30 enters the right atrium 16 through the superior vena cava 32 while blood from the lower parts of the body enters the right atrium 16 through the inferior vena cava 34. The blood is pumped from the right atrium 16, to the right ventricle 20, and to the lungs (not shown) to be oxygenated. Blood returning from the lungs enters the left atrium 18 via the pulmonary veins 36 and is pumped into the left ventricle 22. Blood leaving the left ventricle 22 enters the aorta 38 and flows into the left subclavian artery 40, the left common carotid 42, and the brachiocephalic trunk 44, including the right subclavian artery 46 and the right common carotid 48.

With respect to the implanted circulatory assist device 10, two cannulae 50, 52 (inflow and outflow, respectively) extend between cardiovascular structures and a pump 54. The pump 54 may be any implantable or extracorporeal pump that is radially- and/or axially-driven. Those skilled in this art, however, recognize that other types of pumps may be used in other embodiments and may include pumps such as those described in U.S. application Ser. No. 11/627,444, entitled HEART ASSIST SYSTEM and published as U.S. Application Publication No. 2007/0197854, the disclosure of which is incorporated herein by reference in its entirety. Still other pumps may include those that are commercially-available, such as the SYNERGY Pocket Micro-Pump from CircuLite Inc. (Saddle Brook, N.J.).

A cable 56 may extend transdermally from the pump 54 to a position in the abdomen where the cable 56 exits the patient 14 and connects to a power supply (not shown). Suitable power supplies may include a universal-type power supply that sends power to the pump 54 via the cable 56, such as a rechargeable battery pack.

The inflow cannula 50 may include a distally-positioned tip 62 that is configured to extend through a wall of the heart 12 or, more specifically as shown in FIG. 1, through the apex 64 and into the left ventricle 22. The outflow cannula 52 may extend from an outflow port 51 of the pump 54 to the aorta 38 and is secured with one or more sutures 53.

Figure 2:
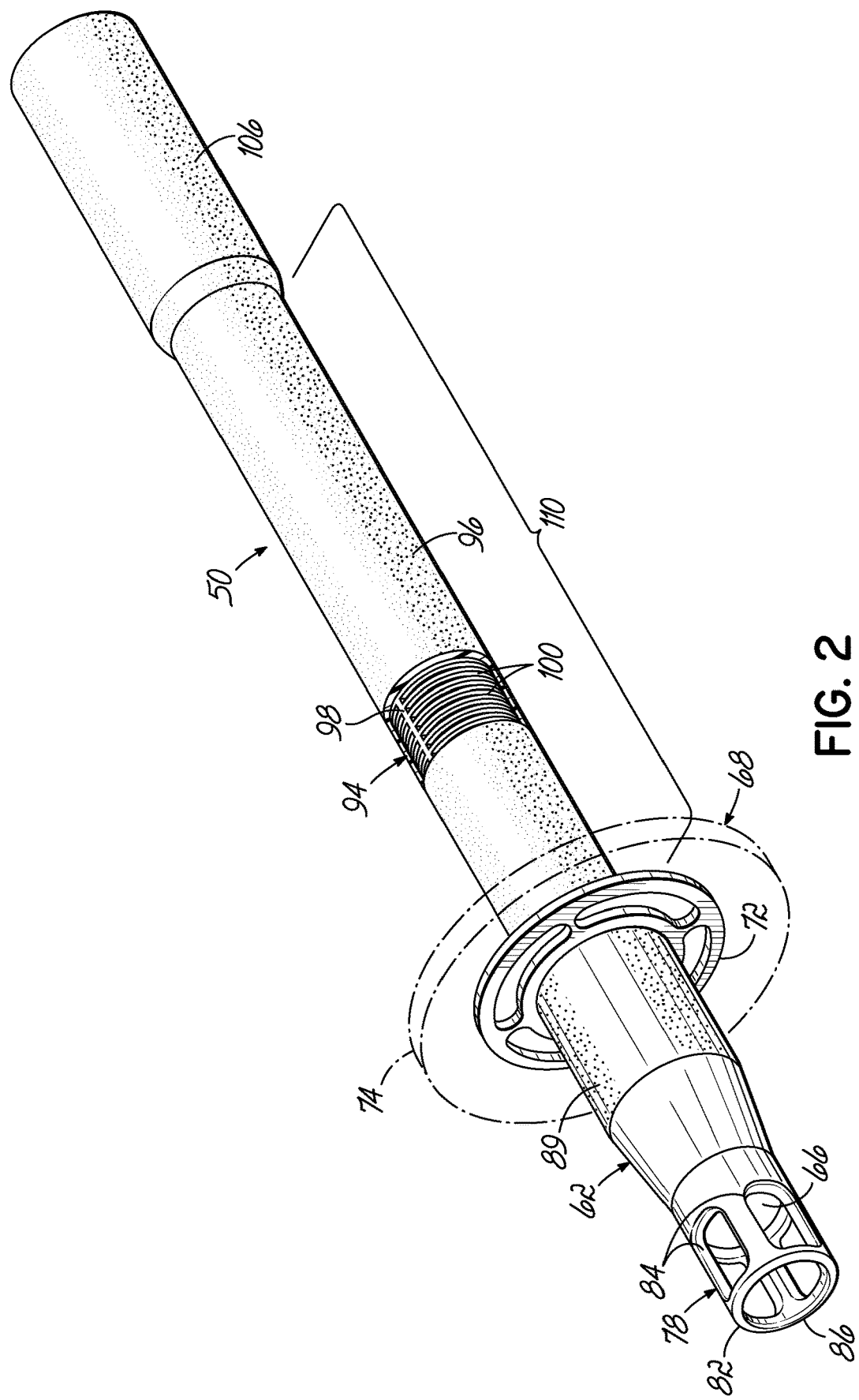
FIG. 2 is a perspective view of the cannula of FIG. 1 with a portion of a jacket removed to illustrate a malleable member constructed in accordance with one embodiment of the present invention.

Turning now to FIG. 2, additional details of the inflow cannula 50 and the tip 62 are described with greater detail. While only the inflow cannula 50 is described in such detail, it would be understood that the outflow cannula 52 may include similar construction and features as the inflow cannula 50 or would be otherwise constructed in a manner that is known to those of ordinary skill in the art. The tip 62 may be constructed from a metallic material, such as titanium, a titanium alloy, stainless steel, or platinum having a sintered section or at least a portion covered by a fabric to promote and control the in-growth of tissue. Alternatively, the tip 62 may be molded from a thermoset material, such as silicone, or a thermoplastic material, such as polyurethane. An example of a polyurethane that may be used is CARBOTHANE (Lubrizol Advanced Materials, Inc., Cleveland, Ohio). If a relatively conformable design is desired, the tip 62 may be constructed from a material having a durometer ranging from about shore 25A to about shore 90A. If a relatively rigid design is desired, the tip 62 may be constructed from a material having a durometer ranging from about shore 55D to about shore 90D.

To minimize the chance of thrombus formation, an insert molding process may be used to eliminate parting lines on the tip 62, i.e., those places where a mismatch of material may occur. Use of the insert molding process results in a luminal surface 66 that is smooth and seamless for direct contact with blood flowing through the tip 62. Accordingly, it may not be necessary to coat the luminal surface 66 of the tip 62 with an anti-thrombotic material. These coatings may, however, be included if so desired.

To increase hemocompatibility of metallic-constructions, the tip 62 may be polished to minimize irregularities resulting from the machining process. The highly polished surface minimizes the proliferation of cells, hence minimizing the likelihood that tissue will grow over the tip 62 and occlude blood flow through the tip 62 and into the inflow cannula 50. Alternatively, or additionally, the tip 62 may include a tissue in-growth band 89 to limit and/or control cell growth relative to the tip 62. The tissue in-growth band 89 may be constructed from a porous polymeric material, such as expanded polytetrafluoroethylene ("ePTFE"), a woven polyester fabric tubing (e.g., DACRON brand of polyester fabric), velour, or other like material that creates a scaffolding to which cells adhere.

The tip 62 may include certain structures and features that are configured to further reduce occlusion of the tip 62 and the inflow cannula 50. For example, in FIG. 3, the tip 62 includes a distally-positioned cage 78 having a distally-positioned ring 82 and a plurality of openings 84 extending proximally from the ring 82. The openings 84 permit blood to be continuously withdrawn from the left ventricle 22 (FIG. 1) into the tip 62, even when a distal tip end 86 of the cage 78 becomes obstructed or occluded, such as by the mitral valve chordae 89 (FIG. 1) or adjacent wall tissue of the heart 12. The tip 62 may also include one or more barbs 90 configured to couple and retain the inflow cannula 50 to the tip 62. Accordingly, the distal end of the inflow cannula 50 should be sufficiently flexible so as to slide over the barbs 90 of the tip 62.

Referring still to FIGS. 1 and 2, the tip 62, as shown, is secured to the apex 64 of the heart 12. Suitable methods for securing the tip 62 may include, for example, one or more purse string sutures, one or more deployable anchors (such as those described in U.S. application Ser. No. 12/256,911, entitled TRANSSEPTAL CANNULA, TIP, DELIVERY SYSTEM, AND METHOD and published as U.S. Application Publication No. 2009/0112050), a cannula securement device (such as those described in U.S. application Ser. No. 12/917,525, entitled CANNULA STABILIZER and published as U.S. Application Publication No. 2011/0118668), or, as shown, with an attachment ring 68 (FIG. 1). In some embodiments of the present invention, the attachment ring 68 may be similar to the devices described in U.S. Application Ser. No. 61/531,957, entitled CANNULA TIPS, TISSUE ATTACHMENT RINGS, AND METHODS OF DELIVERING AND USING THE SAME, which was filed on Sep. 7, 2011. The disclosure of each application is incorporated herein by reference, in its entirety.

Figure 3:
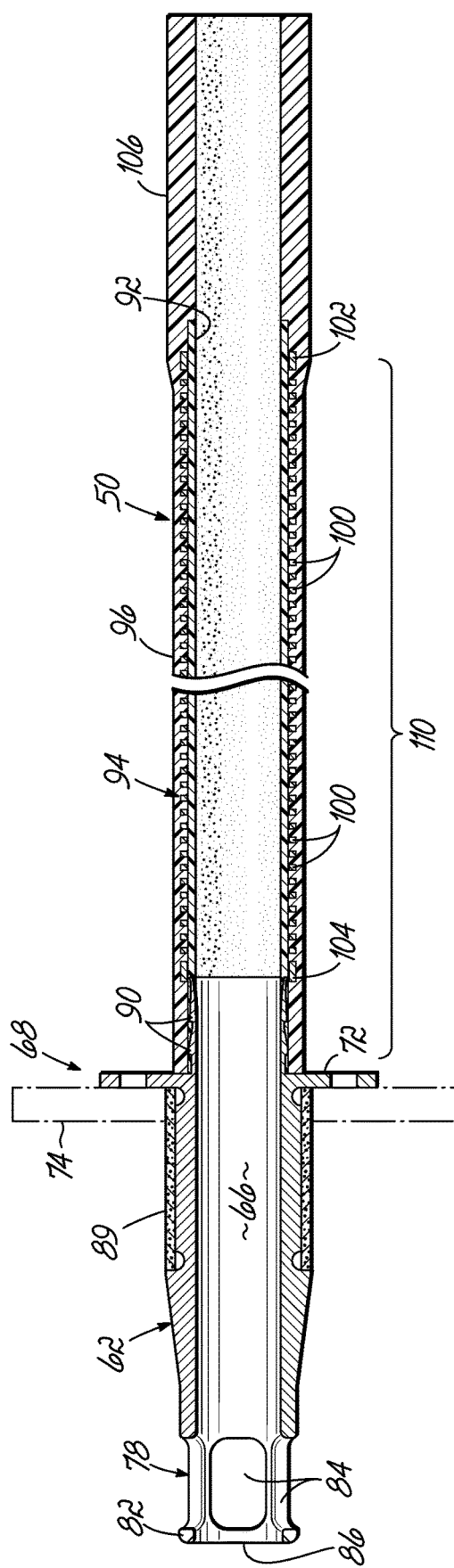
FIG. 3 is a cross-sectional view of the cannula of FIG. 1.
Figure 4:
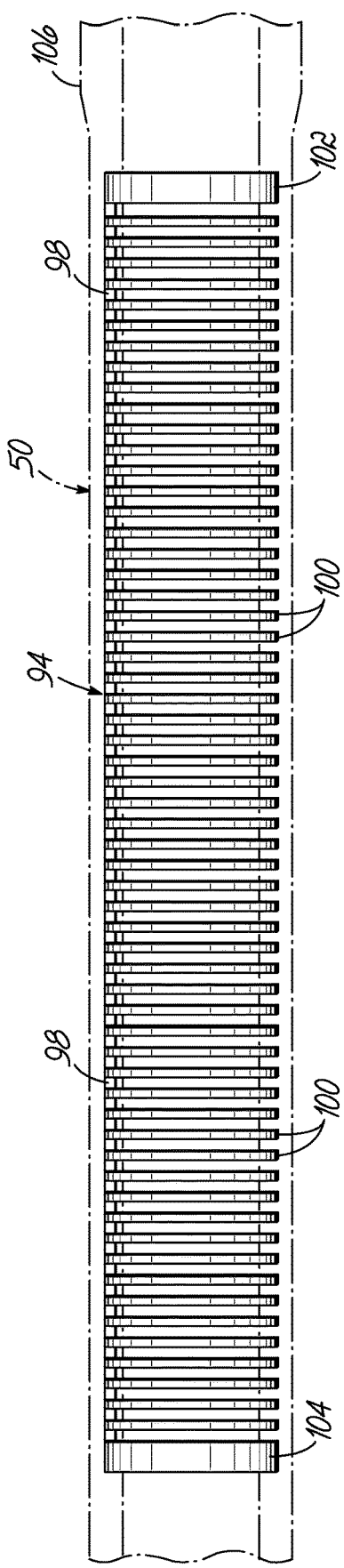
FIG. 4 is a side-elevational view of the malleable member of FIG. 2, shown in a straight configuration, with the cannula environment shown in phantom.

With reference to FIGS. 3 and 4, the inflow cannula 50 and the attachment ring 68 are shown and described in greater detail. The illustrated attachment ring 68 includes a rigid portion 72 and a tissue in-growth band 74 that is coupled to the rigid portion 72. The rigid portion 72, with the tissue in-growth band 74, includes a lumen (not shown) that is configured to receive the tip 62 as described in detail below.

The tissue in-growth band 74 may be constructed from a material that is similar to those described previously with respect to the tissue in-growth band 89 of the tip 62. The rigid portion 72 is configured to be sutured through the tissue in-growth band 89 to an outer surface of the apex 64. The tip 62 of the inflow cannula 50 is inserted through the attachment ring 68 and the muscle comprising the wall of the apex 64 and into the left ventricle 22.

Referring still to FIGS. 3 and 4, the inflow cannula 50, itself, may be constructed in a manner similar to any suitable intravascular cannula device. This may include, for example, a liner portion 92 constructed from materials such as an extruded aliphatic, polycarbonate-base polyurethane, aliphatic polyether polyurethane, aromatic polyether polyurethane, aromatic polycarbonate-based polyurethane, silicone-modified polyurethane, or silicone. Antimicrobial agents may be embedded within the material prior to the forming process to effectively reduce or eliminate the presence of bio-film and reduce the potential for infection. Alternatively, the antimicrobial agent may be applied after the molding process is complete. However, the liner 92 is not required.

A malleable member 94, according to one embodiment of the present invention, surrounds the liner 92 and may be encased between the liner 92 and a jacket 96 constructed from polymeric materials similar to the listing of materials for the liner 92. The malleable member 94 is configured to provide the inflow cannula 50 with a degree of plasticity allowing the physician to bend and shape the inflow cannula 50 to fit the patient's anatomy without breakage. While not required, the malleable member 94 may be positioned along a medial portion 110 of the inflow cannula 50 so that the proximal and distal ends of the inflow cannula 50 remain sufficiently flexible for coupling to the pump 54 (FIG. 1) and the tip 62, respectively.

With the malleable member 94, the inflow cannula 50 is configured to retain the desired shape without relaxing into an unformed and loose shape. In that regard, and as shown in the illustrative embodiment, the malleable member 94 includes a strut 98 (for example, a longitudinal strut 98) that extends the length of the malleable member 94 and is generally parallel to a lengthwise central axis of the cannula 50. A plurality of transverse struts 100, illustrated as successive rings, extends laterally away from the longitudinal strut 98. Said another way, the longitudinal strut 98 extends along a longitudinal lengthwise direction of the malleable member 94 and may form a unitary structure with, and is tangential to, the plurality of transverse struts 100. Proximal and distal struts 102, 104 may terminate the respective ends of the plurality of transverse struts 100 and may also be formed as a unitary structure with the longitudinal strut 98 and/or the plurality of transverse struts 100. The proximal and distal struts 102, 104, having a width dimension that is generally greater than the width dimension of the transverse struts 100, which further anchors the malleable member 94 within the jacket 96.

In some embodiments, the plurality of transverse struts 100 may have a constant pitch, e.g., a number of struts per unit of longitudinal distance; however, in other embodiments, the pitch may vary along the longitudinal length of the inflow cannula 50 so as to vary a malleableness of the cannula 50. For example, and in accordance with one embodiment of the present invention, the malleable member 94 may be constructed with a first portion having struts spaced at a first pitch and a second portion having struts spaced at a second pitch, the first pitch being greater than the second pitch. The resultant cannula would exhibit less shape control in the first portion as compared to the second portion.

The malleable member 94, being configured to assume and retain the desired shape without fracturing, may be constructed from any suitably malleable material, that is, a material that is generally bendable, formable, or pliable without fracture or breakage. Exemplary materials may include, for example, annealed steel, MP35N, or other metallic materials. If radiopacity is desired for in vivo visualization under fluoroscopy or echocardiogram, the malleable material may be comprised of a highly dense material, such as tantalum or gold, or incorporate radiopaque materials therein. In still other embodiments of the present invention, the malleable member 94 may be constructed from metallic tubing, such as a hypotube, that is laser or otherwise cut to the desired configuration.

The inflow cannula 50, having the malleable member 94 as described above, may be positioned, and will retain, various configurations. As shown in FIGS. 4A-5B, the inflow cannula 50 may be placed in a straight configuration, for example, such as would be the packaged configuration during shipment and before a surgical use. As necessary or desired, the physician may manipulate the inflow cannula 50 from the straight configuration to a bent configuration in which at least one portion of the inflow cannula 50 is deflected in at least one direction away from the longitudinal lengthwise axis of the cannula 50.

The configurability of the inflow cannula 50, however, may be limited. For example, FIGS. 4A and 4B illustrate the relative range of motion of the malleable member 94 in an upwardly-directed bend (FIG. 4A) and in a downwardly-directed bend (FIG. 4B). More specifically, the illustrative malleable member 94 inherently provides a greater range of motion in the upwardly-directed bend as compared with the downwardly-directed bend. As the inflow cannula 50 is bent downwardly, as shown in FIG. 4B, the angle of deflection is limited by the relative spacing of the plurality of transverse struts 100. Accordingly, the amount of deflection may be limited by the distance separating adjacent ones of the plurality of transverse struts 100 (e.g., the pitch) as well as the thickness of each of the plurality of transverse struts 100.

Figure 5A:
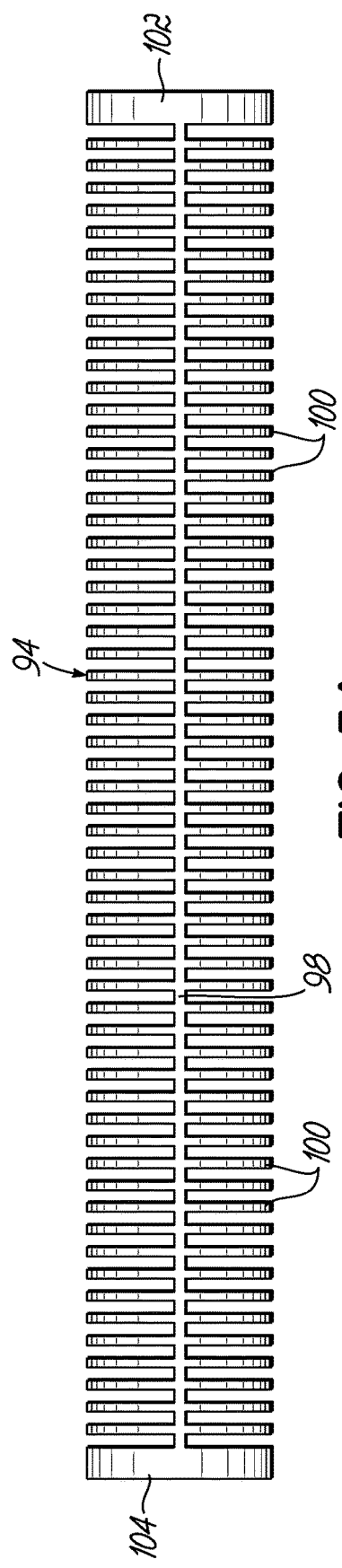
FIG. 5A is a top view of the malleable member of FIG. 3, shown in a straight configuration.
Figure 5B:
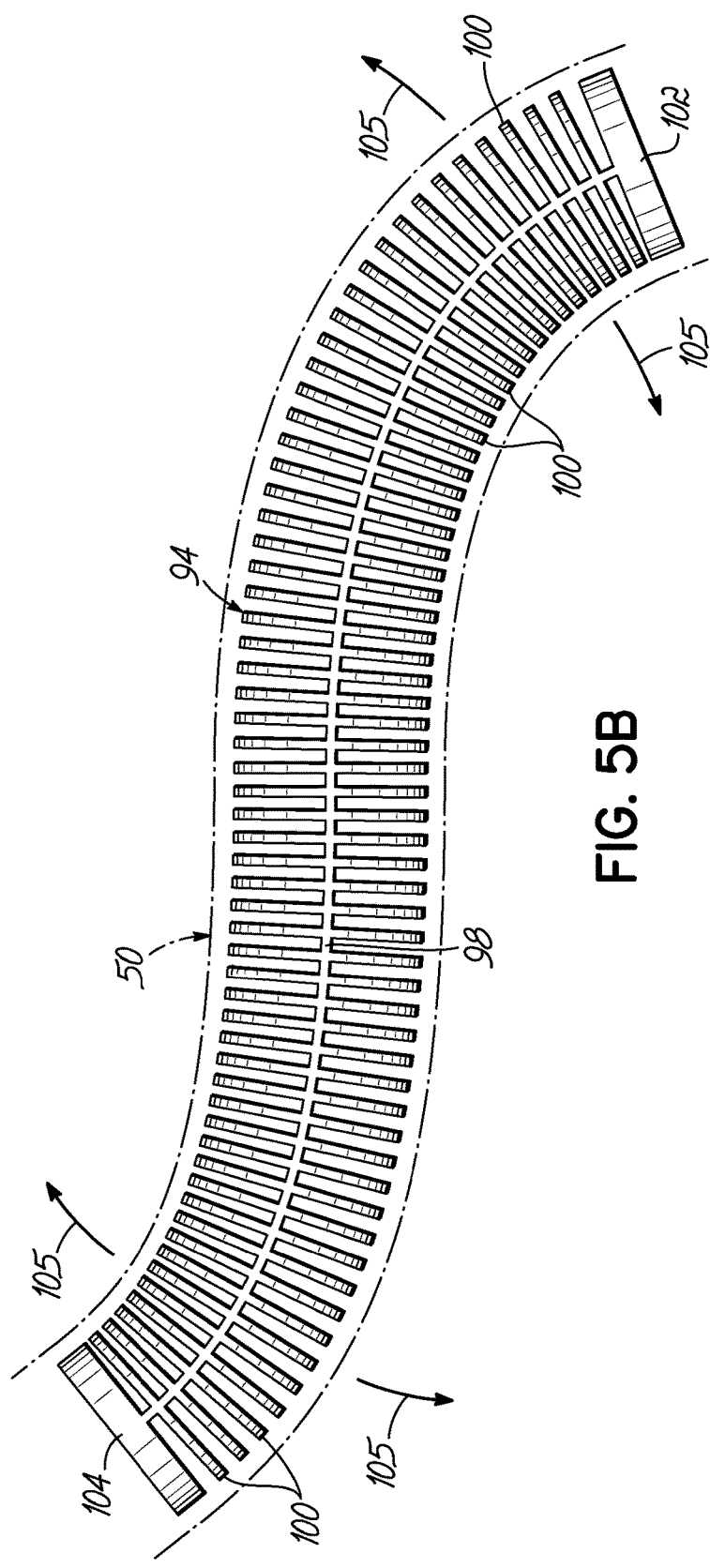
FIG. 5B is a top view of the malleable member of FIG. 3 bent in a lateral serpentine configuration, with the cannula environment shown in phantom.

FIG. 5B illustrates a similar limitation in the range of motion for the inflow cannula 50. However, the movement of the inflow cannula 50 shown in FIG. 5B is in a lateral, serpentine direction, as indicated by arrows 105, and not along an axial direction shown in FIGS. 4A and 4B.

Returning again to FIGS. 2 and 3, additional features of the malleable member 94 and the inflow cannula 50 are shown and described in detail. In this particular embodiment of the present invention, the inflow cannula 50 includes a proximal hub 106 configured to be coupled to an inflow port 108 (FIG. 1) of the pump 54 (FIG. 1). Accordingly, the material comprising the proximal hub 106 of the inflow cannula 50, whether the material is the liner 92, the jacket 96, or both, may be thickened to provide an outer diameter at the hub 106 that is larger than the outer diameter of the remaining portion (for instance, the medial portion 110) of the inflow cannula 50. The hub 106 should be sufficiently flexible so that physician may slide the hub 106 onto the receiving inflow port 108 (FIG. 1) of the pump 54 (FIG. 1).

In use, and with reference to FIG. 1, the physician may bend or otherwise shape the inflow cannula 50 before, during, or after the tip 62 is coupled or otherwise secured to the apex 64 of the heart 12. The shape may depend, at least in part, on the anatomy of the particular patient 14 and the position selected for the pump 54. In FIG. 1, the inflow cannula 50 is configured into an "L" shape such that the tip 62 aligns, generally perpendicularly, with the apex 64 and the left ventricle 22 while the proximal hub 106 is aligned, generally collinearly, with the inflow 108 of the pump 54 within the abdominal cavity of the patient 14. While not illustrated herein, without the malleable member 94 (FIG. 2), the inflow cannula 50 would otherwise relax into an unconstrained and loose shape in which the medial portion 110 falls, or dangles, below the inflow 108 of the pump 54. With the malleable member 94, the inflow cannula 50 retains the designated shape until and unless the physician further manipulates or otherwise bends the inflow cannula 50.

Figure 6:
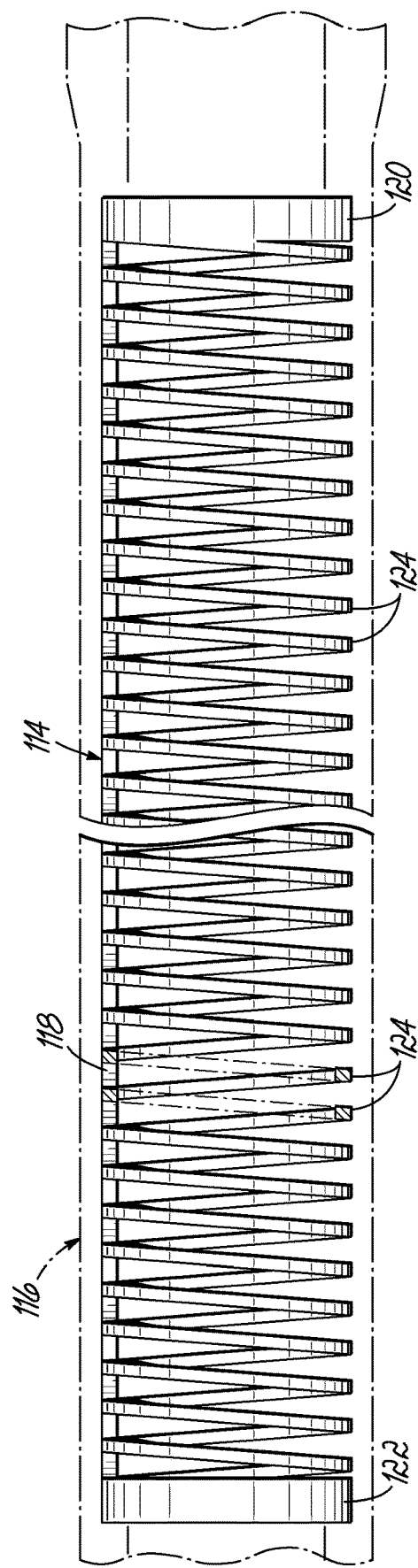
FIG. 6 is a side-elevational view of a malleable member in accordance with another embodiment of the present invention, with the cannula environment shown in phantom.

In accordance with another embodiment of the present invention, and with reference to FIG. 6, a malleable member 114 for use in a cannula 116 may include a strut 118 positioned parallel to the lengthwise central axis of the cannula 116. Proximal and distal struts 120, 122 extend from the strut 118 in a manner that is similar to the malleable member 94 of FIG. 2. However, in FIG. 6, the malleable member 114 further includes a continuous, helical strut 124 that is coupled to the strut 118 tangentially along one side of the helical strut 124. The helical strut 124 may be constructed, for example, as a coil. Although not required, the helical strut 124 may terminate proximally and distally with the proximal and distal struts 120, 122, respectively, so as to provide a unitary structure construction. Alternatively, the proximal and distal struts 120, 122 may be formed separately from the helical strut 124 and then welded or otherwise secured thereto. The proximal, distal, and/or helical struts 120, 122, 124 may be formed as a unitary structure with the longitudinal strut 118, if desired, to reduce movement of the struts 120, 122, 124 relative to one another, which could result in damage to the cannula material.

The helical strut 124 of FIG. 6 enables greater range of motion and configuration of the cannula 116 as compared to the inflow cannula 50 of FIG. 4A. The increased motion, or greater degree of deflection, may be due, at least one part, to the coil-like configuration of the helical strut 124 in which the likelihood that adjacent ones of the struts 124 will make contact is reduced.

Figure 7:
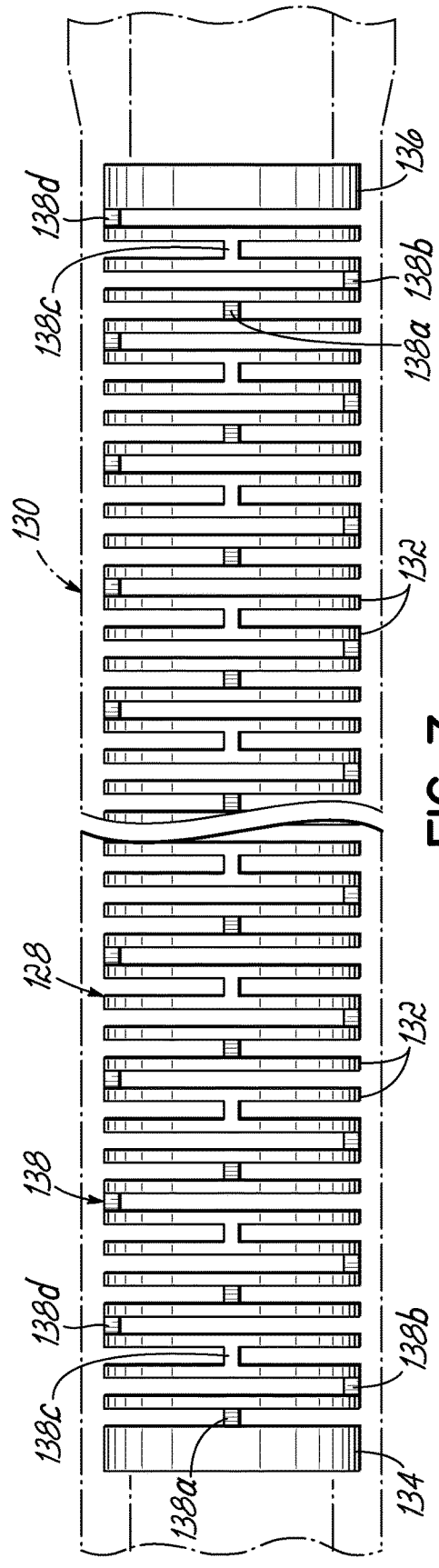
FIG. 7 is a side-elevational view of a malleable member in accordance with yet another embodiment of the present invention, with the cannula environment shown in phantom.

Still another embodiment of the present invention is directed to a malleable member 128 for use with a cannula 130 and is shown in FIG. 7. The malleable member 182 includes a plurality of transverse struts 132 with distal and proximal struts 134, 136 that are similar to those of the malleable member 94 of FIG. 2. However, the illustrative malleable member 128 includes a segmented strut 138 that extends in a direction that is parallel to the lengthwise central axis of the cannula 130. More particularly, the segmented strut 138 is discontinuous in that each successive segment 138a, 138b, 138c, 138d is circumferentially displaced about the transverse struts 132 relative to an adjacent segment 138a, 138b, 138c, 138d. The segments 138a, 138b, 138c, 138d are, therefore, spaced in at least two circumferential positions along the malleable member 128, which may be, but is not limited to, 180 degrees apart. If three circumferential positions are used, then adjacent segments may have circumferential positions that are spaced about 120 degrees apart. Generally, the circumferential spacing of adjacent segments may be determined by dividing 360 degrees by the number of segment positions desired. In the illustrative embodiment of FIG. 7, four segment positions are used and would be preferentially spaced by about 90 degrees. However, one of ordinary skill in the art would readily appreciate that the spacing of segments need not be uniform or limited by the method of determination described herein.

Similar to the malleable member 114 of FIG. 6, the malleable member 128 is sufficiently malleable to permit a wide range of motion and deflection without limiting motion a particular direction. Yet, the cannula 130 is sufficiently stable to retain the formed shape designated by the physician.

While the present invention has been illustrated by a description of various illustrative embodiments and while these embodiments have been described in some detail, it is not the intention of the Applicants to restrict or in any way limit the scope of the appended claims to such detail. Additional advantages and modifications will readily appear to those skilled in the art. The various features of the invention may be used alone or in any combination depending on the needs and preferences of the user. However, the invention itself should only be defined by the appended claims.

What is claimed is:

1. A malleable cannula for moving blood from a chamber of the heart of a patient to a heart pump, the malleable cannula comprising:
    a polymeric jacket having proximal and distal ends, wherein the proximal end is configured to be coupled to the heart pump; and
    a malleable member surrounded by the jacket, the malleable member having a proximal end, a distal end, and a lumen extending therebetween and along a lengthwise axis of the malleable cannula, the lumen being configured to transfer blood from the chamber of the heart to the heart pump, the malleable member including a longitudinal strut extending parallel to the lengthwise axis and a plurality of non-helical transverse struts coupled to and extending laterally from the longitudinal strut and around at least a portion of the lumen, the malleable member configured to assume and maintain a formed shape of the malleable cannula,
    wherein the longitudinal strut is discontinuous along a lengthwise dimension thereof and is comprised of a plurality of spaced apart segments.

2. The malleable cannula of claim 1, wherein the malleable member further comprises:
    a proximal strut coupled to and extending laterally from the longitudinal strut at a proximal end of the malleable member, the proximal strut extending at least partially around the lumen; and
    a distal strut coupled to and extending laterally from the longitudinal strut at a distal end of the malleable member, the distal strut extending at least partially around the lumen,
    wherein the proximal and distal struts have a width dimension that is greater than a width dimension of the non-helical transverse struts of the plurality to further anchor the malleable member within the jacket.

3. The malleable cannula of claim 2, wherein the proximal strut, the distal strut, and the plurality of non-helical transverse struts are constructed as a unitary structure.

4. The malleable cannula of claim 3, wherein the unitary structure further includes the longitudinal strut.

5. The malleable cannula of claim 1, wherein the malleable member is constructed from a metallic tube.

6. The malleable cannula of claim 1, wherein the malleable member is constructed from annealed steel, MP35N, tantalum, gold, or a combination thereof.

7. The malleable cannula of claim 1, wherein the plurality of non-helical transverse struts includes a plurality of successive rings.

8. The malleable cannula of claim 1, wherein the non-helical transverse struts of the plurality are spaced apart by a pitch.

9. The malleable cannula of claim 1, further comprising:
a tip coupled to a distal end of the malleable cannula and configured to extend through a biological tissue.

10. The malleable cannula of claim 1, wherein each of the plurality of segments is located at one of a number of circumferential positions about the plurality of non-helical transverse struts, the number of circumferential positions being greater than 1.

11. The malleable cannula of claim 10, wherein a select one of the plurality of segments is circumferentially displaced from an adjacent one of the plurality of segments by 360 degrees divided by the number of circumferential positions about the plurality of non-helical transverse struts.

12. The malleable cannula of claim 1, further comprising:
a liner coupled to an inner surface of the lumen of the malleable member.

13. The malleable cannula of claim 1, wherein each of the plurality of segments is circumferentially displaced from an adjacent one of the plurality of segments and about the plurality of non-helical transverse struts.

14. A malleable cannula for moving blood from a chamber of the heart of a patient to a heart pump, the malleable cannula comprising:
a polymeric jacket having proximal and distal ends, wherein the proximal end is configured to be coupled to the heart pump; and
a malleable member surrounded by the jacket, the malleable member having a proximal end, a distal end, and a lumen extending therebetween and along a lengthwise axis of the malleable cannula, the lumen being configured to transfer blood from the chamber of the heart to the heart pump, the malleable member including a longitudinal strut extending parallel to the lengthwise axis and a plurality of transverse struts coupled to and extending laterally from the longitudinal strut and around at least a portion of the lumen, the malleable member configured to assume and maintain a formed shape of the malleable cannula, wherein the malleable member further comprises:
a proximal strut coupled to and extending laterally from the longitudinal strut at a proximal end of the malleable member, the proximal strut extending at least partially around the lumen; and
a distal strut coupled to and extending laterally from the longitudinal strut at a distal end of the malleable member, the distal strut extending at least partially around the lumen,
wherein the proximal and distal struts have a width dimension that is greater than a width dimension of the traverse struts of the plurality to further anchor the malleable member within the jacket,
wherein the longitudinal strut is discontinuous along a lengthwise dimension thereof and is comprised of a plurality of spaced apart segments.

* * * * *